United States Patent
Janik

(10) Patent No.: US 10,918,775 B2
(45) Date of Patent: Feb. 16, 2021

(54) APPARATUS AND METHOD FOR CARRYING OUT AN ISONATREMIC DIALYSIS

(71) Applicant: B. BRAUN AVITUM AG, Melsungen (DE)

(72) Inventor: Waldemar Janik, Melsungen (DE)

(73) Assignee: B. BRAUN AVITUM AG, Melsungen (DE)

(*) Notice: Subject to any disclaimer, the term of this patent is extended or adjusted under 35 U.S.C. 154(b) by 203 days.

(21) Appl. No.: 16/037,702

(22) Filed: Jul. 17, 2018

(65) Prior Publication Data
US 2019/0022292 A1    Jan. 24, 2019

(30) Foreign Application Priority Data
Jul. 18, 2017 (DE) .......... 10 2017 116 097

(51) Int. Cl.
*A61M 1/16* (2006.01)
*A61M 1/36* (2006.01)

(52) U.S. Cl.
CPC .......... *A61M 1/1605* (2014.02); *A61M 1/165* (2014.02); *A61M 1/1617* (2014.02);
(Continued)

(58) Field of Classification Search
CPC .. A61M 1/1605; A61M 1/1617; A61M 1/165; A61M 1/1656; A61M 1/3609;
(Continued)

(56) References Cited

U.S. PATENT DOCUMENTS 3,993,945 A * 11/1976 Warmoth ............... G01N 27/07
324/449
6,126,831 A  10/2000 Goldau et al.
(Continued)

FOREIGN PATENT DOCUMENTS

DE     19734992 C1   10/1998
DE  102013108543 A1   2/2015
(Continued)

OTHER PUBLICATIONS

De Paula et al., "Clinical Consequences of an Individualized Dialysate Sodium Prescription in Hemodialysis Patients", Kidney International, vol. 66 (2004)—pp. 1232-1238.
(Continued)

*Primary Examiner* — Dirk R Bass

(57) ABSTRACT

An apparatus and a method for extracorporeal blood treatment, especially for hemodialysis, wherein blood of a patient is flushed with a dialysate in a dialyzer and wherein a variable correlated with the plasma sodium concentration of the blood is measured. The composition of the dialysate then is adjusted in response to the variable measured so that the plasma sodium concentration of the blood at least at the end of the blood treatment has the same value as at the beginning. For measuring the variable correlated with the plasma sodium concentration of the blood, for example a bypass operation can be implemented in which the dialysate is guided past the dialyzer so that a residual volume on the side of the used dialysate at least partially adopts the concentration of the substances dissolved on the blood side.

16 Claims, 6 Drawing Sheets

(52) U.S. Cl.
CPC ........ *A61M 1/1656* (2013.01); *A61M 1/3609* (2014.02); *A61M 2205/3317* (2013.01); *A61M 2205/3324* (2013.01); *A61M 2205/502* (2013.01)

(58) Field of Classification Search
CPC .. A61M 2205/3317; A61M 2205/3324; A61M 2205/502
See application file for complete search history.

(56) References Cited

U.S. PATENT DOCUMENTS

| | | | |
|---|---|---|---|
| 6,267,722 B1* | 7/2001 | Anderson | G01N 21/474 600/300 |
| 2013/0116650 A1 | 5/2013 | Vantard et al. | |
| 2013/0237896 A1* | 9/2013 | Meibaum | A61M 1/361 604/5.04 |
| 2015/0045713 A1 | 2/2015 | Attalah et al. | |
| 2018/0140761 A1* | 5/2018 | Rovatti | A61M 1/1609 |

FOREIGN PATENT DOCUMENTS

| | | |
|---|---|---|
| EP | 0407737 A1 | 1/1991 |
| WO | 2017080969 A1 | 5/2017 |
| WO | 2017080970 A1 | 5/2017 |

OTHER PUBLICATIONS

European Search Report for European Application No. 18183941.6, dated Dec. 5, 2018 with translation, 17 pages.
Mendoza et al., "Dialysate Sodium and Sodium Gradient in Maintenance Hemodialysis: A Neglected Sodium Restriction Approach", Nephrol Dial. Transplant (2011), 26—pp. 1281-1287.
Basile et al., "It is Time to Individualize the Dialysate Sodium Prescription", Seminars in Dialysis, 2015, 4 pages.
German Search Report for German Application No. 10 2017 116 097.3, dated Mar. 1, 2018 with translation, 15 pages.

* cited by examiner

APPARATUS AND METHOD FOR CARRYING OUT AN ISONATREMIC DIALYSIS

CROSS REFERENCE TO RELATED APPLICATIONS

This application claims priority to German application DE 10 2017 116 097.3 filed Jul. 18, 2017, the contents of such application being incorporated by reference herein.

FIELD OF THE INVENTION

The present invention relates to an apparatus and a method for extracorporeal blood treatment (e.g. hemodialysis), with a patient's blood being flushed with a so-called dialysate in a dialyzer.

BACKGROUND OF THE INVENTION

It is the objective of a dialysis therapy, apart from detoxication of the blood, to remove excess water accumulating in the body, due to a renal failure underlying dialysis, from the body. This is done by so-called ultrafiltration in which liquid is removed from the blood via a dialyzer.

Conventional dialyzers usually comprise a tubular dialyzer housing having a longitudinal extension, with the interior of the dialyzer having a cross-section which typically does not vary or varies only insignificantly over the entire longitudinal extension. In the interior, capillary membranes arranged in parallel to each other are provided. The capillary membranes jointly form a section of an extracorporeal blood circulation, while the exterior of the capillaries and the interior of the dialyzer housing form a section of a circulation of the dialysate. The two circulations are active in opposite directions and are separated from each other via the semipermeable membranes of the capillaries. An exchange both of water and of substances takes place through said semipermeable membranes. Especially, water and contaminants are withdrawn from the patient's blood. Removal of retention products increasing in diameter or in molecular weight is worse than that of smaller contaminants in dialyzers by diffusive processes via the membranes.

Hemodialysis, hemodiafiltration and high-flux dialysis are utilized, inter alia, as different dialysis techniques. Hemodialysis is based on the principle of compensating concentrations of small-molecular substances of two liquids that are separated by a semipermeable membrane (diffusion). Being separated from the filter membrane, on the one side the blood containing electrolytes such as potassium and phosphate as well as substances usually eliminated with the urine (e.g. urea, uric acid) is provided. On the other side of the membrane, the dialysate comprising a share of electrolytes geared by the particular needs of a patient is provided. In detail, the dialysate consists of high-purity water, a first basic component (e.g. sodium hydrogen carbonate ($NaHCO_3$)) as well as a second acid component. The latter is composed, for example, of sodium chloride (NaCl), potassium chloride (KCl), magnesium chloride ($MgCl_2$), calcium chloride ($CaCl_2$), acetic acid ($CH_3COOH$) and glucose. The semipermeable filter membrane (dialysis membrane) between the blood and the dialysate has pores that are permeable to small molecules such as water, electrolytes and substances usually eliminated with the urine, but withhold large molecules such as proteins and blood cells.

As a rule, metering pumps and conductivity probes are used for preparing and, respectively, proportioning the dialysate. A probe measures the conductivity after addition of the sodium hydrogen carbonate with a first metering pump. Another probe detects the conductivity of the entire dialysate after also the acid component has been added with another metering pump. By way of the measured conductivities then the added amounts are controlled. This method is known as conductivity-controlled proportioning.

In so-called volumetric proportioning the conductivity probes merely serve for checking. In this case, proportioning is carried out directly via the metering pump delivery rates, which requires knowledge about the composition of the components used.

The correct composition of the dialysate plays an important role in dialysis. Especially sodium plays an important role, as it is the most frequently occurring cation both in the dialysate and in the blood plasma. Sodium is absorbed especially in the form of saline (NaCl). An increased intake of sodium can be compensated by supplying a corresponding amount of liquid. However, an increased intake of liquid results in the fact that during the next dialysis cycle more excess liquid has to be withdrawn by ultrafiltration. High ultrafiltration rates in turn require an addition of sodium, however, if drops of the blood pressure occur due to the liquid withdrawal. This in turn entails an increased intake of water. Hence a vicious circle will begin. However, a too low sodium value in the dialysate is not advantageous, either. The intracellular and extracellular spaces are in osmotic balance with each other. A low sodium concentration in the dialysate would result in a decrease of the extracellular osmolarity due to diffusion processes within the dialyzer. Since both spaces are balanced, however, water would flow in an undesired manner from the intracellular space into the extracellular space.

For the afore-mentioned reasons, it is therefore desirable to individually adapt the sodium concentration in the dialysate so that the plasma sodium concentration is changed as little as possible and at best is not changed at all during dialysis. Such dialysis is referred to as isonatremic (see e.g. de Paula, F. M.; Peixoto, A. J.; Pinto, I. V.; Dorigo, D.; Patricio, P. J. M. and Santos, S. F. F.: "Clinical Consequences of an Individualized Dialysate Sodium Prescription in Hemodialysis Patients", Kidney International, 2004, 66, 1232-1238, and Basile, C. and Lomonte, C.: "It is Time to Individualize the Dialysate Sodium Prescription", Seminars in Dialysis, 2016, 29, 24-27).

It would be easiest to collect and to analyze a blood sample prior to each dialysis so as to adjust the sodium concentration in the dialysate on that basis. However, this procedure is very time-consuming and related with great expenditure on apparatuses. For this reason, in many dialysis centers dialysis is carried out with a standardized composition of the dialysate, although the plasma sodium concentration may be different from patient to patient (see Mendoza, J. M.; Sun, S.; Chertow, G. M.; Moran, J.; Doss, S. and Schiller, B.: "Dialysate Sodium and Sodium Gradient in Maintenance Hemodialysis: a Neglected Sodium Restriction Approach?", Nephrol Dial Transplant 2011, 26, 1281-1287).

The afore-mentioned known approaches are disadvantageous to the effect that it is time-consuming to establish the required parameters, that frequently two sensors upstream and downstream of the dialyzer are required including appropriate efforts of calibration and, respectively, that conductivity measurements at the outlet of the used dialysate are influenced by substances arriving from the blood in the used dialysate.

SUMMARY OF THE INVENTION

The object underlying the present invention is, inter alia, to automatically adapt the dialysate as to its composition so that the plasma sodium concentration is maintained or a defined amount of sodium is added to or withdrawn from the patient.

This object is achieved by an apparatus and a method according to the independent claims.

Accordingly, a variable correlated with the plasma sodium concentration of the blood is measured and the composition of the (fresh) dialysate is adjusted depending on the variable measured such that the plasma sodium concentration of the blood at least at the end of the blood treatment has the same value as at the beginning thereof. Measurement can be carried out, for example, by shortly switching the dialysis apparatus to a bypass mode at the beginning of the dialysis therapy so as to then establish, on the side of the used dialysate, a value which strongly correlates with the plasma sodium concentration of the patient. This value will be corrected, where necessary. After that, the dialysis apparatus automatically composes the (fresh) dialysate so that the plasma sodium concentration is reduced, increased or remains constant corresponding to the established and possibly corrected value.

In other words, apparatus and a corresponding method for extracorporeal blood treatment are provided, especially for hemodialysis, comprising a dialyzer to which fresh dialysate can be supplied via a supply line of the dialysate, and from which used dialysate can be discharged via a discharge line of the dialysate, a bypass line which connects the supply line and the discharge line of the dialysate, thereby bypassing the dialyzer, and which can selectively be opened for short circuiting the dialyzer, a first measuring device for measuring a variable correlated with the plasma sodium concentration of the blood to be cleaned in the dialyzer, the first measuring device being provided directly downstream of the dialyzer, and a proportioning unit for automatically adjusting the composition of the dialysate in response to the variable measured such that the plasma sodium concentration of the blood at least at the end of the blood treatment has the same value as at the beginning. Therein, line sections of the supply line and the discharge line of the dialysate located between the bypass line and the dialyzer are pumpless, such that at least at a beginning of the extracorporeal blood treatment the correlated variable is determined via an interposed bypass operation wherein the dialysate remains in the dialyzer.

The suggested solution may provide for a dialysis cycle by which high ultrafiltration rates can be avoided in the medium and long run and the amount of water and electrolytes in the blood is only moderately varied. Furthermore, only little or no equipment at all is required, as the measuring devices suggested here are available already in many conventional dialysis apparatuses.

Specific advantageous embodiments of the present invention are stated in the subclaims.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Hereinafter, preferred embodiments of the present invention are described by the example of an apparatus and a method for carrying out isonatremic dialysis.

Figure 1:
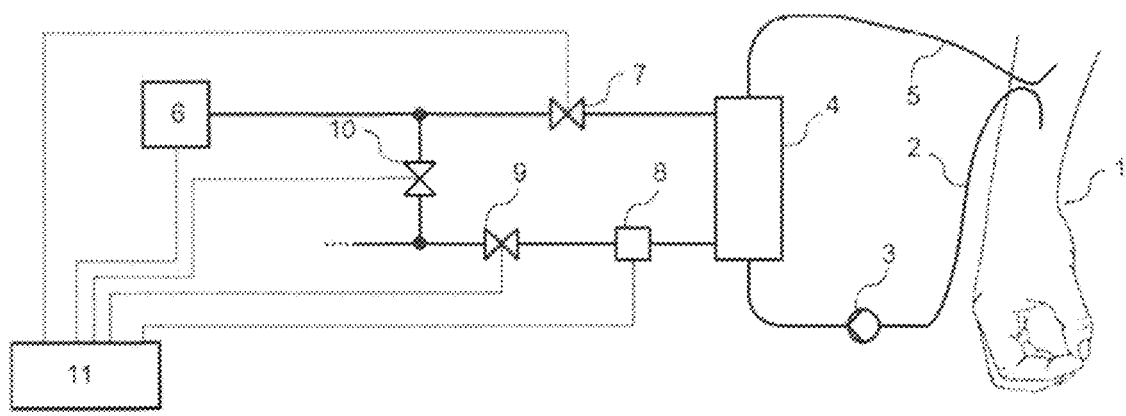
FIG. 1 shows a schematic block diagram of a dialysis apparatus according to a first embodiment.

FIG. 1 illustrates a schematic block diagram of a dialysis apparatus according to a first embodiment.

In this case, blood is withdrawn from a dialysis patient 1 via an arterial tubing system 2 with the aid of a delivery unit (pump) 3. The blood flows into a dialyzer 4 where it is freed from toxins and excess water with diffusion, convection and/or ultrafiltration. Subsequently, the processed blood is refed to the patient 1 via a venous tubing system 5. Withdrawal and refeeding may also be carried out via a joint cannula.

The dialyzer 4 may be, for instance, a commercially available dialyzer as it is utilized for extracorporeal blood treatments. It contains plural hollow fiber capillaries that are further comprising a semipermeable membrane. The patient's blood flows through the capillaries. Inside the dialyzer 4 they are flushed from outside with the fresh dialysate which absorbs toxins and further contaminants from the blood. The fresh dialysate is prepared in a proportioning unit 6. As mentioned already in the beginning, for this purpose various known principles can be employed. Examples hereof are conductivity-controlled proportioning, volumetric proportioning or a mixed form of the two aforementioned. Usually high-purity water, a basic component and an acid component are mixed for this purpose.

In a main connection, the fresh dialysate flows through a first controllable valve 7 into the dialyzer 4, there absorbs the contaminants from the blood and possibly discharges other substances, especially hydrogen carbonate and/or other electrolytes to the blood. After having passed the dialyzer 4, the dialysate is referred to as used dialysate.

In accordance with the following embodiments, the used dialysate passes a measuring device 8 and a second controllable valve 9. A balancing unit (not shown) ensures, for example by comparison and possibly adaptation of the flow of fresh and used dialysates, that exactly the prescribed amount of excess water is withdrawn from the patient. In the main connection furthermore a third controllable valve 10 is closed. A control unit 11 detects at least the measuring values and, respectively, states of the measuring device 8, of the proportioning unit 6 and of the first to third valves 7, 9 and 10. Moreover, the control unit 11 outputs commands to the proportioning unit 6 and to the first to third valves 7, 9 and 10.

Hereinafter, the function of the dialysis apparatus shown in FIG. 1 is illustrated in detail with reference to FIG. 2.

Figure 2:
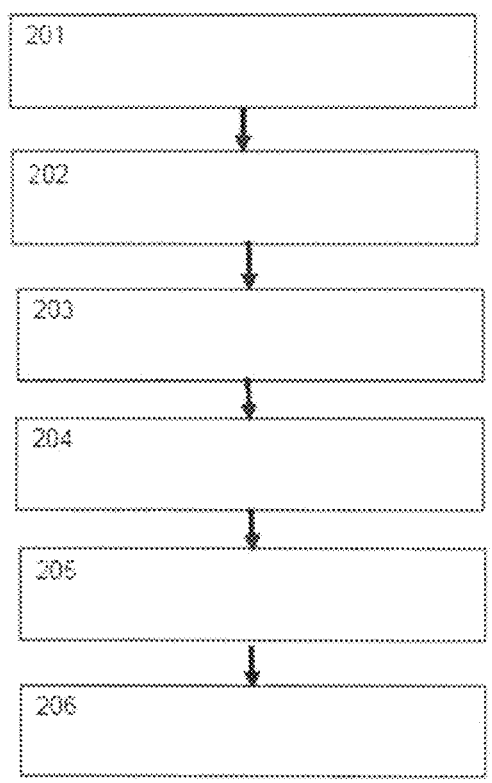
FIG. 2 shows a flow diagram of a dialysis control method according to the first embodiment.

FIG. 2 shows a flow diagram of a dialysis control method according to the first embodiment carried out with the dialysis apparatus.

In step 201, at the beginning of a dialysis treatment, preferably within the first 20 minutes, more preferred within the first 15 minutes, even more preferred within the first 10 minutes, the dialyzer 4 is switched to the bypass. Preferably, the blood flow of the delivery unit 3 corresponds to a prescribed value which is higher than the blood flow when the patient is connected.

During the bypass, the fresh dialysate is guided from the proportioning unit 6 via the third valve 10 opened by the control unit 11 in step 202 past the dialyzer 4 into a drain.

The first and second valves 7, 9 are closed during the bypass. The blood of the patient 1, on the other hand, continues flowing through the dialyzer 4. Restricted by the first and second valves 7, 9, a residual volume of used dialysate is retained on the outlet side of the dialyzer. Strictly speaking, the residual volume of used dialysate is located in the entire section between the valves 7 and 9 including the dialysate side of the (inside the) dialyzer 4. Depending on the blood flow of the delivery unit 3 and on the size of the dialyzer 4, within few minutes the entire or at least part of the residual volume of used dialysate is saturated on the side of the used dialysate in the dialyzer 4 so far that it adopts, completely or at least in part, the concentration of the substances dissolved on the blood side. The considered substances dissolved on the blood side are substances which are sufficiently small for passing through the semipermeable membrane of the dialyzer 4. They include especially free sodium ions and further electrolytes as well as substances usually eliminated with the urine such as urea, uric acid or creatinine.

After terminating the bypass, in step 203 the valve position of the first, second and third valves 7, 9, 10 is switched over so that the (fresh) dialysate from the proportioning unit 6 displaces the at least partially saturated residual volume of the used dialysate from the dialyzer 4. In so doing, the residual volume passes the measuring device 8 where a short-term signal change will occur. It is noted in this context that the measuring device 8 may as well be positioned so that during the bypass it continues being flushed with fresh dialysate (i.e. downstream of the bypass line incorporating the valve 10) and not, as shown in FIG. 1, between the dialyzer outlet and the bypass line. (This is applicable mutatis mutandis to the measuring device 13 according to FIG. 5 described in the following. Also, the measuring device 12 according to FIGS. 4, 5 described in the following may be provided in the direction of flow ahead (upstream) of the bypass line (on the side of the used dialysate)).

The value in the extremum (minimum or maximum) of the signal change strongly correlates with the value given at the blood inlet of the dialyzer 4.

Preferably, the measuring device 8 is a temperature-compensating conductivity cell. The conductivity in the extremum after the end of bypass in that case corresponds to the conductivity of the plasma water and, respectively, of the plasma of the patient 1.

Alternatively, also a substance-specific measuring device such as an ion-selective electrode or an optical measuring device can be employed as measuring device 8 so that the blood-side value can be established non-invasively and directly.

The afore-described bypass method is based, in its main features, on the patent DE 197 34 992 C1 which aims at the determination of the dialysance and is incorporated by reference herein in its entirety.

According to the present embodiments, this method now is further developed so that the dialysate is adapted in its composition with the proportioning unit 6 such that sodium is withdrawn from the patient 1 to such an extent that, toward the end of therapy, the plasma sodium concentration corresponds to the initial concentration (isonatremic dialysis). For this, in step 204 in FIG. 2 the measuring value of the local signal extremum is evaluated and in step 205 is transmitted via the control unit 11 to the proportioning unit 6. The latter mixes the dialysate in step 206 so that the plasma sodium concentration is not changed in the further course of the dialysis or at least toward the end has the same value as at the beginning. In order to be able to trace any changes, the bypass is repeated at regular intervals by the afore-mentioned method steps 201 to 206.

In the afore-described bypass method, during the bypass a diffusive balance has to be reached between the blood side and the side of the used dialysate, however. In the case of low blood flows and large dialyzers, this may take several minutes, however. It has to be emphasized that, due to the stagnant residual volume on the side of the used dialysate, the blood is not purified to a sufficiently efficient extent. Although this is negligible when performing one single bypass, the treatment would have to be prolonged so as to achieve a sufficiently high dialysis dose, however, if plural bypasses are to be performed in the course of the dialysis treatment.

Therefore, according to the embodiments, the bypass time may be reduced by renouncing a diffusive balance between the blood side and the side of the used dialysate. Laboratory measurements have resulted in the fact that already 14 seconds of bypass time are sufficient to generate a signal change after the end of bypass, which corresponds to 50% of a complete saturation.

Figure 3B:
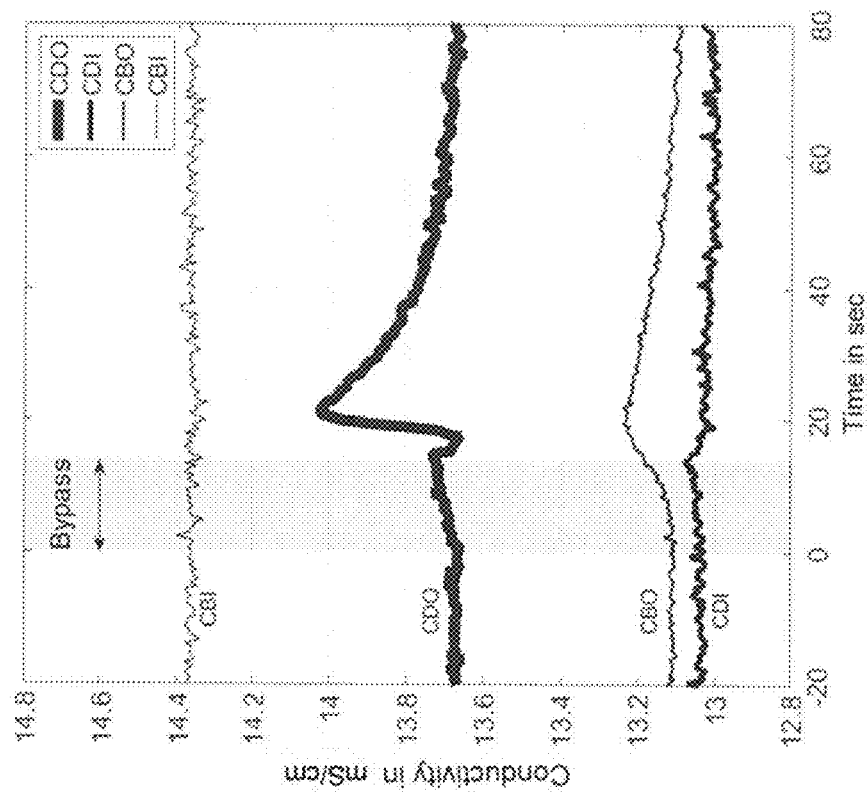
FIGS. 3A and 3B show time diagrams including conductivity curves for longer and, respectively, shorter bypass duration.
Figure 3A:
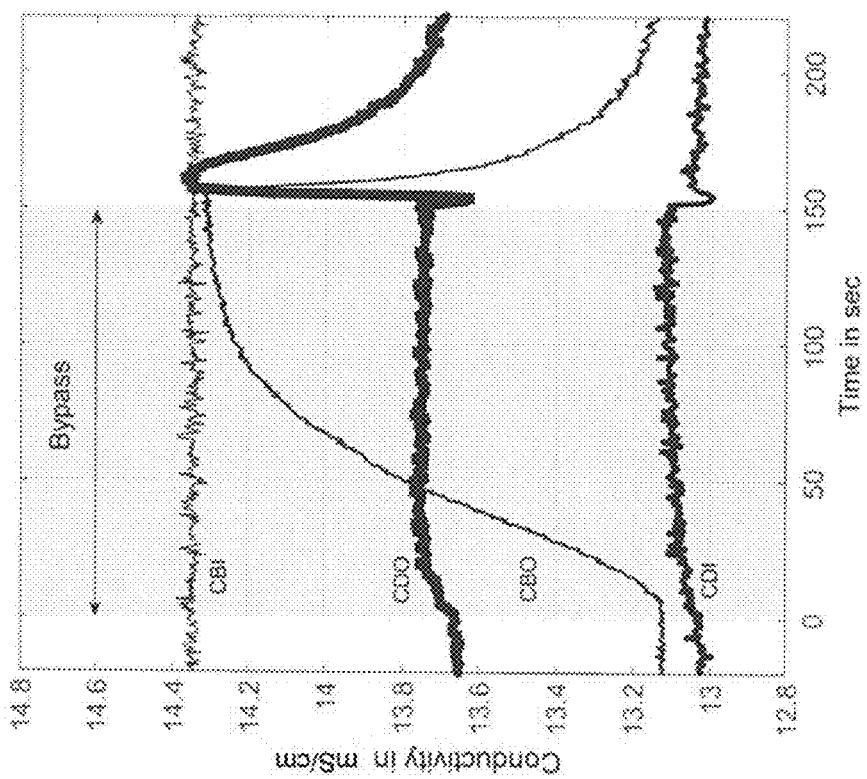

FIGS. 3A and 3B illustrate time diagrams having conductivity curves CBI at the blood inlet (of the dialyzer), CBO at the blood outlet (of the dialyzer), CDI at the dialysate inlet (of the dialyzer) and CDO at the dialysate outlet (of the dialyzer) with longer and, respectively, shorter bypass time for illustrating the afore-mentioned effect, wherein the left-hand diagram corresponds to a bypass with longer duration and the right-hand diagram corresponds to a bypass with shorter duration. The conductivity at the dialysate outlet (of the dialyzer) amounts to about 13.6 mS/cm immediately before performing the bypass. After a bypass duration of 2.5 minutes a complete saturation may be assumed. This is evident also from the fact that the conductivities shown here at the blood inlet and the blood outlet (of the dialyzer) after 2.5 minutes are corresponding to each other and have a value of about 14.4 mS/cm.

The conductivity (CDO) at the dialysate outlet (of the dialyzer) in the extremum after the end of bypass equally amounts to about 14.4 mS/cm, which corresponds to a change of 0.8 mS/cm. It is evident from the right-hand diagram that with a bypass duration of merely 14 seconds the conductivity at the dialysate outlet (of the dialyzer) will increase from 13.6 mS/cm by 0.4 mS/cm to 14.0 mS/cm, which is exactly by half of 0.8 mS/cm.

From the following equation, now the conductivity present at the blood inlet (of the dialyzer) can be concluded:

$$CBI_{calc} = CDO_{pre} + k \cdot (CDO_{ext} - CDO_{pre})$$

$CBI_{calc}$ characterizes the value at the blood inlet (of the dialyzer) non-invasively calculated by the bypass method, $CDO_{pre}$ characterizes the value at the dialysate outlet (of the dialyzer) directly before performing the bypass that is detected by the measuring device 8, and $CDO_{ext}$ characterizes the value in the extremum at the dialysate outlet (of the dialyzer) after the end of bypass. Said values may as well be filtered values. For example, they can be the mean value or median of a defined time segment. The factor k for a 14 second bypass with a mean dialyzer size and a mean blood flow equals 2. If other blood flows or dialyzers or dialysate flows should be used, also an adjustment of the factor k may be carried out. For this, at first a sufficiently long bypass is performed, wherein a diffusive balance between the blood side and the dialysate side can be assumed. Promptly, preferably within 1 to 2 minutes after termination of the long bypass, then a short bypass with a duration of 14 seconds or with different durations is performed. Alternatively, the order may also be changed.

By comparing the measuring values of both bypasses the factor k is subsequently established. For example, the following quotient can be established:

$$k = \frac{\langle CDOext - CDOpre \rangle_{long}}{\langle CDOext - CDOpre \rangle_{short}}$$

The numerator is the difference of the corresponding values from the long bypass and the denominator is the difference of the corresponding values from the short bypass.

In the following, a second embodiment will be described.

Figure 4:
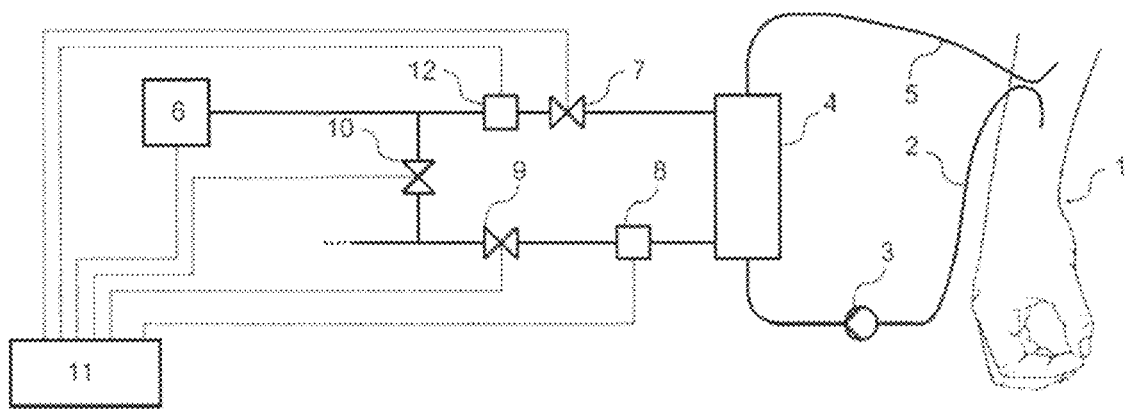
FIG. 4 shows a schematic block diagram of a dialysis apparatus according to a second embodiment.

FIG. 4 shows a schematic block diagram of a dialysis apparatus according to the second embodiment.

In the second embodiment, in the supply line of the fresh dialysate another measuring device 12 is provided, wherein the two measuring devices 8, 12 may be of the same type. The measuring device 12 may as well be a component of the proportioning unit 6, as the latter frequently includes already an appropriate measuring device. Preferably, also the further measuring device 12 is a temperature-compensating conductivity probe. The further measuring device 12 is not compulsory for carrying out an isonatremic dialysis. However, in combination with the measuring device 8 it may be used to facilitate the evaluating algorithm of the signal at the measuring device 8. By way of comparison of the measuring values at both measuring devices 8, 12, it is quickly evident whether after terminating a bypass the extreme value is a minimum or a maximum. When the value at the measuring device 8 is higher or, respectively, lower than that at the further measuring device 12, after the end of bypass a maximum or minimum is sought.

In the following, a third embodiment will be described.

Figure 5:
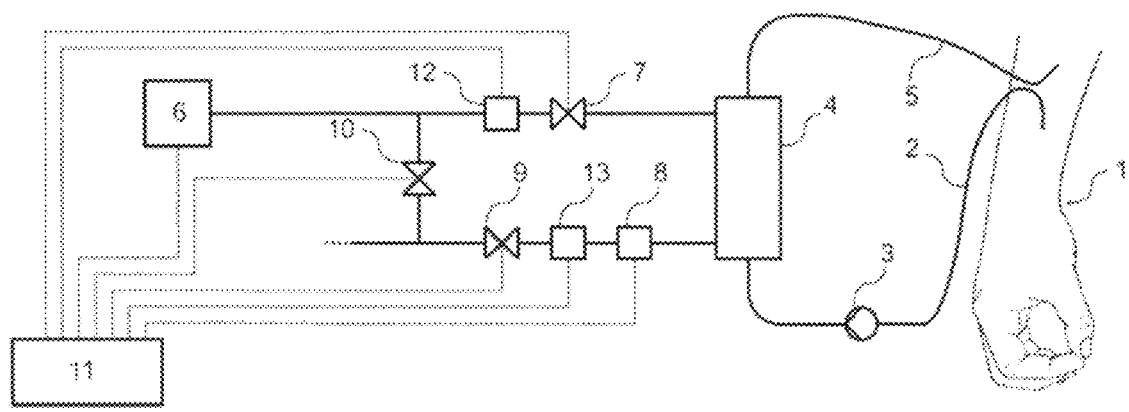
FIG. 5 shows a schematic block diagram of a dialysis apparatus according to a third embodiment.

FIG. 5 shows a schematic block diagram of a dialysis apparatus according to the third embodiment.

As already mentioned, the measuring device 8 preferably is a temperature-compensating conductivity probe. Although sodium and the anions thereof, especially chloride and hydrogen carbonate, constitute those substances in liquids such as dialysate or plasma water which contribute most strongly to the conductivity, the conductivity measurement is influenced by further substances so that a simple conversion between conductivity and sodium concentration is not possible. For example, increased potassium values may increase the conductivity. However, there are also substances which are not conductive per se, but still are adapted to impair the conductivity. It may be exemplified that the addition of non-conductive glucose may reduce the conductivity of an otherwise conductive solution, as glucose impairs the mobility of the conducting ions. Similar effects are caused by toxins and other substances usually eliminated with the urine. Especially at the beginning of a dialysis treatment, a plurality of said substances are passing through the semipermeable membrane in the dialyzer 4 and in this way arrive at the dialysate side. The measuring device 8 therefore measures a conductivity that may be reduced due to said substances. If, however, the proportioning unit 6 would mix exactly said conductivity, in this way sodium would be withdrawn from the patient in the course of the dialysis treatment in an undesired manner. For counteracting said effect it is necessary to correct the conductivity at the measuring device 8. A rigid correction of the conductivity by adding a fixed amount is detrimental, however, as the contamination with toxins may be different from patient to patient and from treatment to treatment.

Therefore, in the third embodiment, a third measuring device 13 is provided at the (dialyzer) outlet of the used dialysate next to the measuring device 8, with the third measuring device 13 serving for determining the toxin contamination of the used dialysate. Preferably, this is an optical sensor measuring the absorption characteristic of the used dialysate. Preferably, the absorption characteristic is measured in the ultraviolet range of between 235 nm and 400 nm. Further preferred, the absorption characteristic of light having a wavelength of 285±15 nm is measured. Alternatively, also an enzymatic or another electrochemical sensor is imaginable.

For correcting the conductivity established with the bypass method the absorption characteristic of the used dialysate immediately before carrying out a bypass can be considered. Alternatively, also the absorption characteristic after terminating the bypass is imaginable which occurs simultaneously with the signal extremum at the measuring device 8.

One possible absorption characteristic is the extinction. Accordingly, the conductivity is corrected by mathematically combining the conductivity and the extinction. In the simplest case, this may be based, for example, on the following linear equation:

$$CBIcalc,korr = a \cdot CBIcalc + b \cdot E + c$$

with CBIcalc,korr characterizing the calculated conductivity at the blood inlet corrected on the basis of measurement by the measuring device 8, a and b being factors, E representing the extinction measured by the third measuring device 13 at the (dialyzer) outlet of the used dialysate and c being a constant.

Now a description of a fourth embodiment based on a neuronal network will follow.

Figure 6:
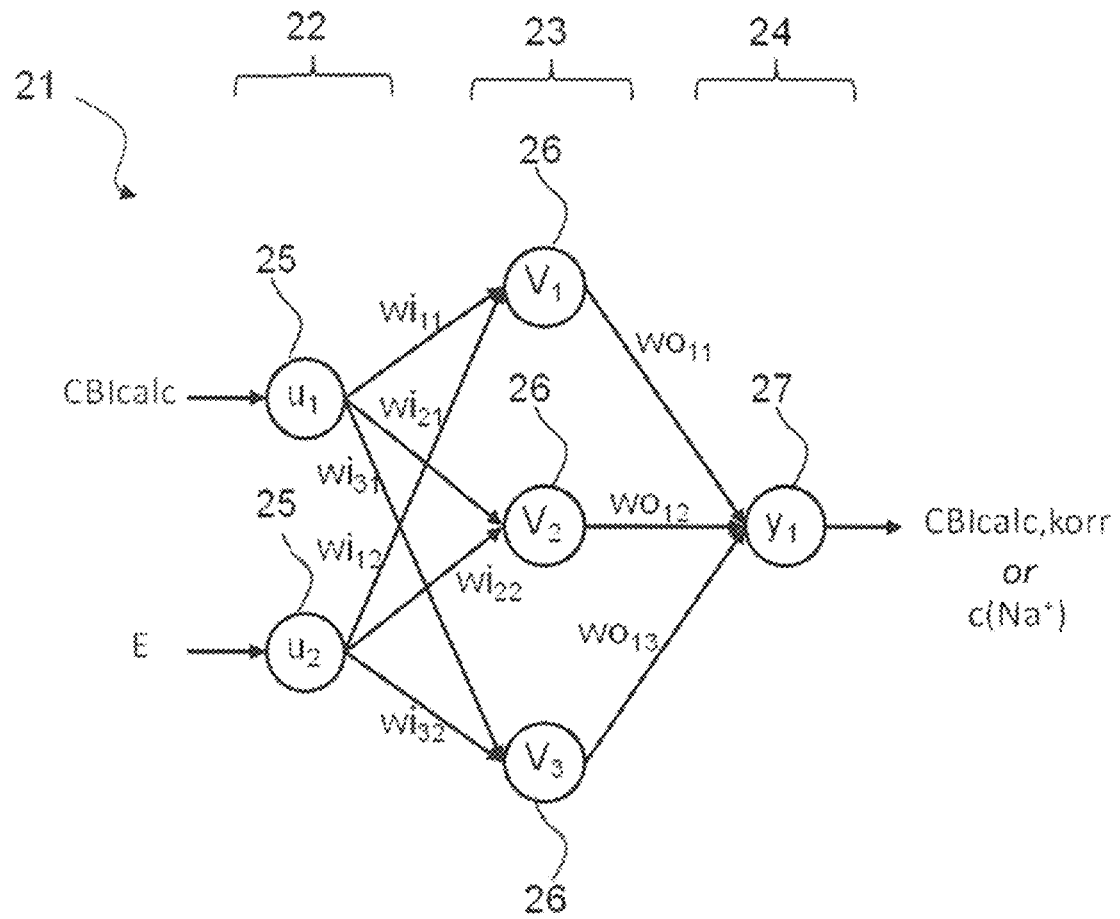
FIG. 6 shows a schematic diagram of a neuronal network for a dialysis apparatus according to a fourth embodiment.

FIG. 6 illustrates a schematic diagram of the neuronal network for a dialysis apparatus according to the fourth embodiment.

Tests have shown that especially artificial neuronal networks achieve very good results. Artificial neuronal networks are able to approximate almost all measurable functions with any accuracy. Usually, they consist of one input layer, at least one concealed layer and one output layer.

FIG. 6 shows such neuronal network 21. An input layer 22 in this case contains two neurons 25 in which as input variables the values for the calculated conductivity at the blood inlet (CBIcalc) and the extinction (E) are standardized. Weighted by the weightings wi, they are transmitted to the intermediate layer neurons 26 of an intermediate layer 23 where the weighted inputs u are added up according to the following formula:

$$\sigma_j = \sum_{k=1}^{r} w_{ijk} u_k$$

Apart from said inputs, there may be employed further constant inputs, so-called threshold values. Threshold values may be either −1 or +1 and may also be weighted. It is moreover possible to feed in also other measuring values of other, e.g. also external measuring devices, as inputs. (Further inputs might be e.g. the conductivity at the dialysate inlet and/or dialysate outlet. Even further inputs might be the potassium and hydrogen carbonate concentrations in the plasma).

For example, it is also imaginable to include e.g. commercially available hematocrit sensors. In addition, it is obvious to consider not only rigid measuring values but also variations of measuring values. Examples hereof are variations of the established conductivities and/or absorption characteristics and/or hematocrit values and/or variations of the relative blood volume and/or of the oxygen saturation of the blood between at least two bypasses.

The sums of the weighted inputs are subsequently transmitted, in each intermediate layer neutron, to a sigmoid activating function. Basically, any sigmoid functions are imaginable. Of preference, a hyperbolic tangent function may be used which excels by the fact that its functional values for any input values are within a range of between the values −1 and +1. The hyperbolic tangent function is defined as follows:

$$g(\sigma) = \frac{e^\sigma - e^{-\sigma}}{e^\sigma + e^{-\sigma}} = \frac{e^{2\sigma} - 1}{e^{2\sigma} + 1} = 1 - \frac{2}{e^{2\sigma} + 1}$$

The output values V of the intermediate layer neurons 26 thus are resulting as follows:

$$V_j = g(\sigma_j) = g\left(\sum_{k=1}^{r} wi_{jk} u_k\right)$$

Finally, output values are provided with output weightings wo and are forwarded to an output neuron 27 of an output layer 24, where a sum is formed. In this case, too, a weighted threshold value may be added.

Thus, the following is resulting as output $y_1$ for the output neuron 27:

$$y_1 = \left(\sum_{j=1}^{s} wo_{1j} V_j\right) + bo_1$$

wherein $bo_1$ represents the weighted threshold value of the output neuron 27.

It is referred to the fact that the threshold values are not shown in FIG. 6.

The network output is the corrected calculated conductivity at the blood inlet which was determined by the bypass method non-invasively at the (dialyzer) outlet of the used dialysate with the measuring device 8. It is also possible, as a matter of course, to arrange for a sodium concentration c(Na$^+$) which is present at the blood inlet to be output directly. Alternatively, also metering delivery rates for the proportioning unit 6 or mixing ratios may be established.

The values for $CBI_{calc,korr}$ and, respectively, c(Na$^+$), i.e. the conductivity and, respectively, sodium concentration, now are provided for performing an isonatremic dialysis also for the dialysate and can be mixed by the proportioning unit 6.

Figure 7:
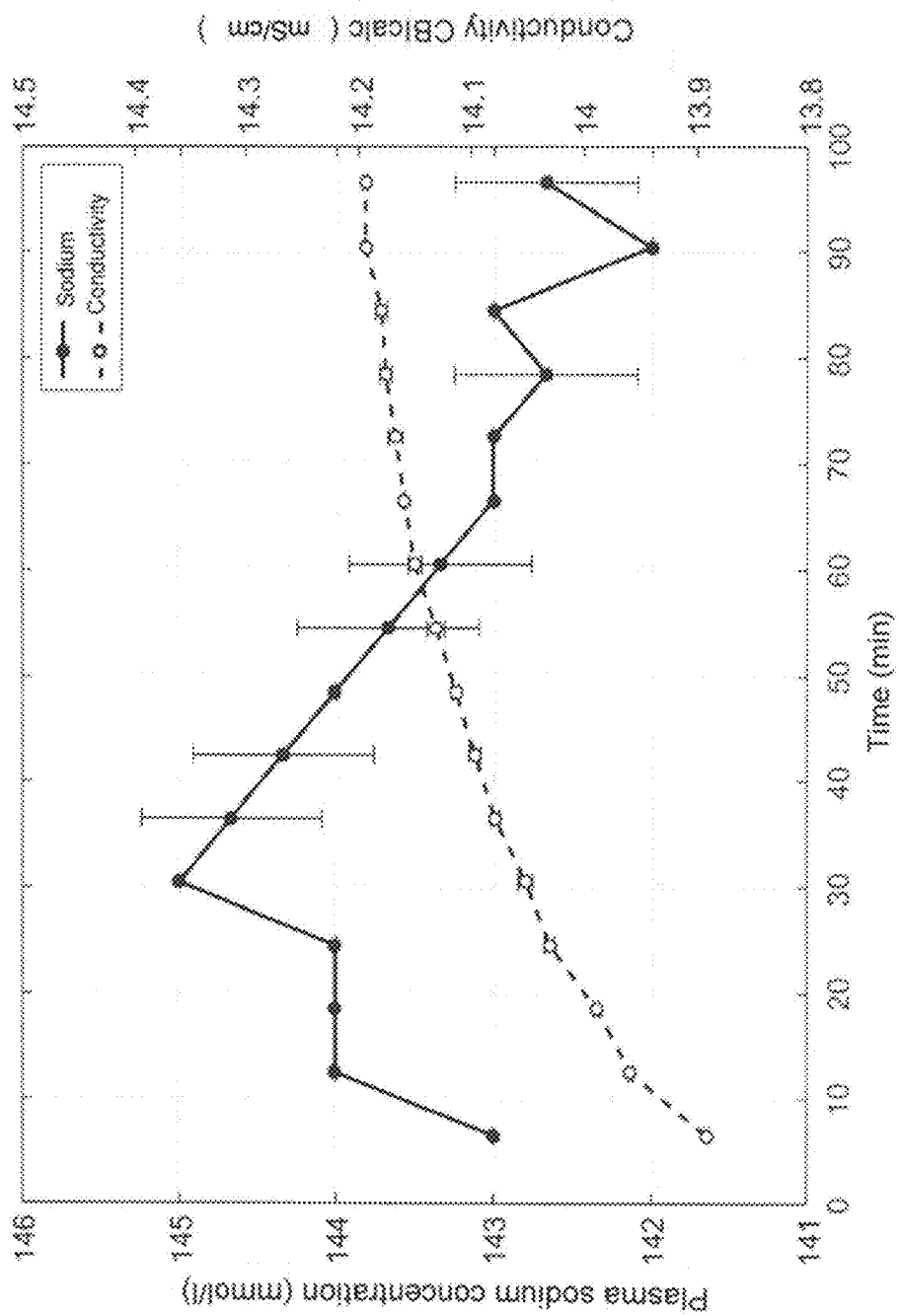
FIG. 7 shows a time diagram including concentration and conductivity curves in the dialysis apparatus according to the fourth embodiment.

FIG. 7 illustrates a time diagram including a concentration and conductivity curve in the dialysis apparatus according to the fourth embodiment as a result of dialysis carried out in the afore-mentioned way. For this purpose, 6 l of fresh blood were dialyzed. The plasma sodium concentration amounted to 143 mmol/l at the beginning of dialysis. In the course of the treatment, the concentration slightly increases, but then gradually drops to 142.7±0.6 mmol/l. The conductivity $CBI_{calc}$ calculated by the bypass method at the beginning amounted to approx. 13.9 mS/cm. This value and the pertinent first extinction were input to the neuronal network. The network then calculated a value of 14.2 mS/cm as a corrected conductivity. Said value was transmitted to the control unit 11, which resulted in the fact that the proportioning unit 6 mixed the dialysate in such manner that within the latter a sodium concentration of 143 mmol/l was obtained. When applied to the total conductivity of the dialysate, 143 mmol/l correspond to approx. 14.2 mS/cm.

Figure 8:
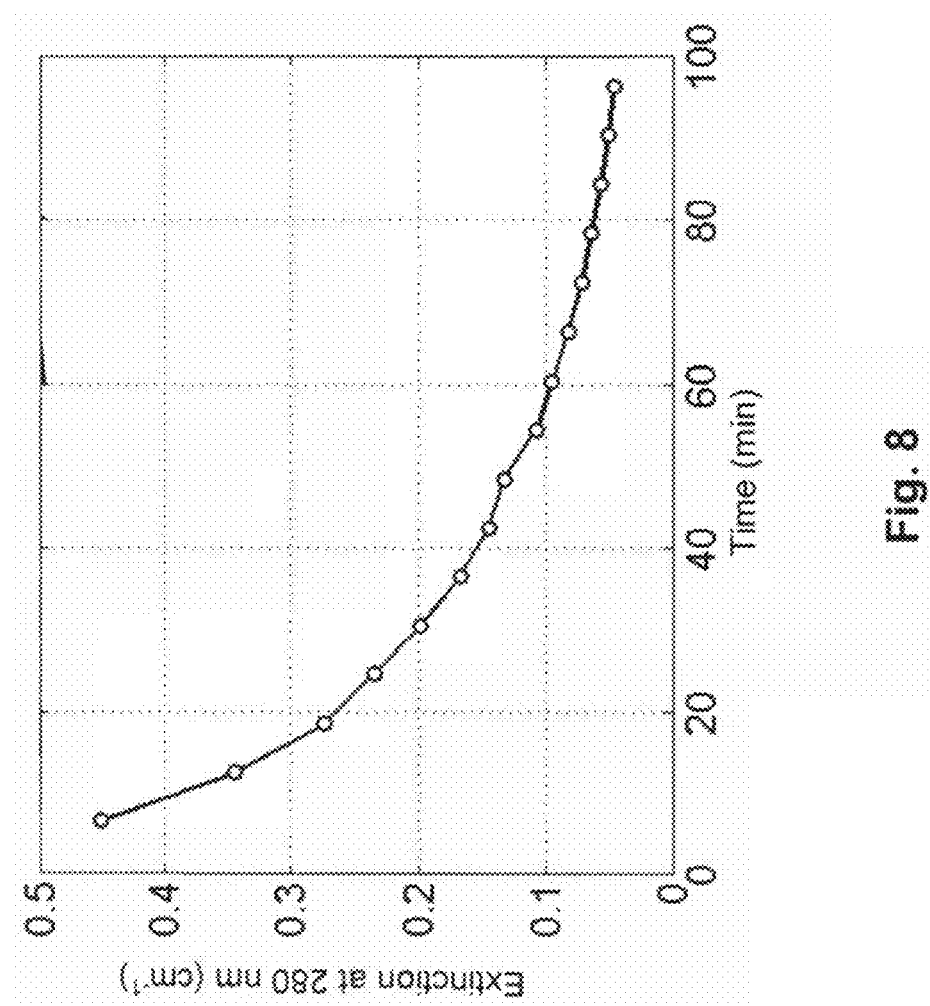
FIG. 8 shows a time diagram including an extinction curve in the dialysis apparatus according to the fourth embodiment.

FIG. 8 illustrates a time diagram including the pertinent extinction curve in the dialysis apparatus according to the fourth embodiment. The emission wavelength of the optical sensor of the third measuring device 13 in this case amounted to 280 nm.

As a matter of course, it is also possible to adjust the fresh dialysate after initially establishing the plasma sodium concentration so that a defined amount of sodium will be withdrawn from or administered to the patient 1. Moreover, the suggested method allows for determining the absolute amount of sodium withdrawn. With a known ultrafiltration volume and the knowledge of the plasma sodium concentration in the course of the dialysis treatment, the withdrawn amount of sodium corresponds to the product of ultrafiltration volume and plasma sodium concentration.

In order to render the method transparent for the medical staff and/or the user, data of the measuring devices and/or characteristics of the dialysate mixed by the proportioning unit 6 may be displayed on a screen or a data management system. This relates especially to conductivities, concentrations, extinctions, pH values, temperatures and pressures.

Moreover, data may be made available as a recommendation only. In this way, the medical staff members may decide on their own, based on said recommended data, whether or not the recommendation is to be followed. Consequently, hypo-, iso- or hypernatremic dialysis need not take place automatically.

Provisions may be made for the weightings of the neuronal network or the factors a and b and the constant c to be established and adjusted ex works. However, it is also possible to configure said values to be adjustable and, respectively, learnable. By way of example, the plasma sodium concentration is referred to which can be established e.g. in a routine laboratory test of the patient's blood shortly before the beginning of the dialysis treatment. The medical staff and/or the user can input said measured value directly to the dialysis apparatus or into a data management system. Then said value will be compared to the calculated value. The calculated value then may be replaced with the measured value, where appropriate. At the same time, the aforementioned weightings and factors can be newly established and adapted by the dialysis apparatus or by the data management system.

Further, collected data may be stored on a patient's card, in the dialysis apparatus and/or in a data management system. Studies carried out in the past few years have resulted in the fact that the plasma sodium concentration of a patient is relatively constant as compared to other parameters (so-called set point theory).

The data stored, especially the calculated conductivity $CBI_{calc}$ and the corrected calculated conductivity $CBI_{calc,corr}$ as well as the plasma sodium concentration $c(Na^+)$ established therefrom can be evaluated with the descriptive statistics (e.g. mean value, standard deviation, time correlation etc.) so as to identify possible variations, which might be indicative of a general change in the state of health.

Summing up, an apparatus and a method for extracorporeal blood treatment have been described, wherein blood of a patient is flushed with a dialysate in a dialyzer and wherein a variable correlated with the plasma sodium concentration of the blood is measured. The composition of the dialysate then is adjusted in response to the variable measured so that the plasma sodium concentration of the blood at least at the end of the blood treatment has the same value as at the beginning. For measuring the variable correlated with the plasma sodium concentration of the blood, for example a bypass operation may be installed in which the dialysate is guided past the dialyzer so that a residual volume on the side of the used dialysate at least partially adopts the concentration of the substances dissolved on the blood side.

The invention claimed is:

1. An apparatus for extracorporeal blood treatment, the apparatus comprising:
   a dialyzer coupled to a supply line to receive dialysate and to a discharge line to pass the dialysate;
   a bypass line coupled between the supply line and the discharge line that bypasses the dialyzer, the bypass line selectively opened during an interposed bypass operation to short circuit the dialyzer with the dialysate remaining in the dialyzer;
   a first measuring device configured to measure a variable after the interposed bypass operation from the dialysate that remained in the dialyzer, such that the variable is correlated with a plasma sodium concentration of blood to be cleaned in the dialyzer, the first measuring device downstream of the dialyzer;
   a control unit configured to implement the interposed bypass operation with valves to guide the dialysate past the dialyzer with longer and shorter durations so that a residual volume at least partially adopts the concentration of the substances dissolved on a blood side of the dialyzer, to supply the residual volume to the first measuring device for measuring the variable correlated with the plasma sodium concentration of the blood, to configure the first measuring device to measure the conductivity of the residual volume associated with the longer and shorter durations of the bypass operation, and to establish by comparison of the measured results a factor to apply to measurements after the shorter duration to calculate the conductivity of the plasma or plasma water at an inlet of the dialyzer on the basis of measured conductivities of the dialysate in the discharge line before and after the interposed bypass operation; and
   a proportioning unit coupled to the control unit, the proportioning unit configured to automatically adjust a composition of the dialysate in the supply line in response to the measured variable and the factor established by the comparison of the measured results to apply to measurements after the shorter duration such that the plasma sodium concentration of the blood at least at an end of the extracorporeal blood treatment has the same value as at a beginning of the extracorporeal blood treatment;
   wherein line sections of the supply line and the discharge line located between the bypass line and the dialyzer are pumpless, such that at least at the beginning of the extracorporeal blood treatment the variable correlated with the plasma sodium concentration of the blood is determined during the interposed bypass operation with the dialysate remaining in the dialyzer.

2. The apparatus according to claim 1, wherein the proportioning unit is configured to adjust the composition of the dialysate in response to the measured variable so that during the blood treatment the plasma sodium concentration of the blood is reduced, increased or maintained substantially constant.

3. The apparatus according to claim 1, wherein the first measuring device comprises at least one of a conductivity measuring device, a substance-specific measuring device, or an optical measuring device.

4. The apparatus according to claim 3, wherein the first measuring device comprises a temperature-compensating conductivity cell.

5. The apparatus according to claim 1, wherein the bypass operation is implemented within the first 20 minutes of the beginning of the extracorporeal blood treatment.

6. The apparatus according to claim 1, wherein the bypass operation is implemented within the first 15 minutes of the beginning of the extracorporeal blood treatment.

7. The apparatus according to claim 1, wherein the bypass operation is implemented within the first 10 minutes of the beginning of the extracorporeal blood treatment.

8. The apparatus according to claim 1, wherein the proportioning unit adjusts the composition of the dialysate so that sodium is withdrawn from the blood such that the plasma sodium concentration toward the end of the blood treatment corresponds to the initial plasma sodium concentration.

9. The apparatus according to claim 1, further comprising:
   a second measuring device configured to measure a second measurement of the variable correlated with the plasma sodium concentration of the blood in the supply line of the dialysate, wherein the measured value of the second measuring device is compared to the measured value of the first measuring device to determine whether a measured extreme value corresponds to a maximum or a minimum.

10. The apparatus according to claim 1, further comprising:
    a third measuring device configured to measure a toxin contamination of the dialysate in the discharge line, wherein the measured toxin contamination is used for correcting a conductivity measurement of the first measuring device.

11. The apparatus according to claim 10, wherein the third measuring device comprises an optical sensor configured to measure an absorption characteristic of the dialysate in the discharge line.

12. The apparatus according to claim 11, further comprising:
    a neuronal network configured to correct the conductivity measurement of the first measuring device using a sigmoid activating function in an intermediate layer.

13. The apparatus according to claim 12, wherein the sigmoid activating function is a hyperbolic tangent function.

14. A method of extracorporeal blood treatment using a dialyzer; the method comprising the steps of:

supplying dialysate to the dialyzer via a supply line of the dialysate, and discharging the dialysate via a discharge line;

selectively opening a bypass line for longer and shorter durations during an interposed bypass operation which connects the supply line and the discharge line of the dialysate, thereby bypassing the dialyzer for short circuiting the dialyzer so that a residual volume at least partially adopts the concentration of the substances dissolved on a blood side of the dialyzer, line sections of the supply line and the discharge line located between the bypass line and the dialyzer are pumpless;

measuring a variable after the interposed bypass operation from the residual volume for the longer and shorter durations of the interposed bypass operation, such that the variable is correlated with the plasma sodium concentration of blood to be cleaned in the dialyzer by a measuring device provided downstream of the dialyzer, the correlated variable determined via an interposed bypass operation wherein the dialysate remains in the dialyzer at least at a beginning of the extracorporeal blood treatment;

obtaining a factor to calculate the conductivity of the plasma or plasma water at an inlet of the dialyzer on the bases of measured conductivities of the dialysate in the residual volume for the longer and shorter durations of the bypass operation; and adjusting the composition of the dialysate in response to the variable measured and the factor obtained by the comparison of the measured conductivities to apply to measurements after the shorter duration such that the plasma sodium concentration of the blood at least at an end of the extracorporeal blood treatment has the same value as at the beginning.

15. The method according to claim 14, further comprising:

implementing a bypass operation in which the dialysate is guided past the dialyzer so that a residual volume in the discharge line at least partially adopts the concentration of the substances dissolved on the blood side, and measuring the variable correlated with the plasma sodium concentration of the blood in the residual volume in the discharge line.

16. The method according to claim 15, wherein the implemented bypass operation is repeated at regular intervals.

* * * * *